United States Patent [19]

Robson

[11] Patent Number: 4,512,931

[45] Date of Patent: Apr. 23, 1985

[54] INSECTICIDAL PRODUCT AND PREPARATION THEREOF

[75] Inventor: Michael J. Robson, Bracknell, England

[73] Assignee: Imperial Chemical Industries PLC, London, England

[21] Appl. No.: 535,625

[22] Filed: Sep. 26, 1983

[30] Foreign Application Priority Data

Oct. 18, 1982 [GB] United Kingdom ............... 8229724

[51] Int. Cl.³ .......................................... C07C 121/75
[52] U.S. Cl. ................................................ 260/465 D
[58] Field of Search .................................... 260/465 D

[56] References Cited

U.S. PATENT DOCUMENTS 4,133,826 1/1979 Warnant et al. ............... 260/465 D
4,136,195 1/1979 Warnant et al. ............... 424/304
4,183,948 1/1980 Huff .................................... 424/304

FOREIGN PATENT DOCUMENTS 2064528A 6/1981 United Kingdom .

OTHER PUBLICATIONS

Pesticide Science, vol. 11, No. 2, Apr. 1980, pp. 156–164, Society of Chemical Industry, Bentley et al., "Fluorinated Analogues of Chrysanthemic Acid".

Primary Examiner—Dolph H. Torrence
Attorney, Agent, or Firm—Cushman, Darby & Cushman

[57] ABSTRACT

A process is described by which the pair of cyhalothrin isomers represented by (R)-α-cyano-3-phenoxybenzyl (1R,cis)-3-(Z-2-chloro-3,3,3-trifluoroprop-1-en-1-yl)-2,2-dimethylcyclopropane carboxylate and its enantiomer is converted by base catalyzed epimerization in solution into the insecticidally more useful isomer pair represented by (S)-α-cyano-3-phenoxybenzyl (1R,cis)-3-(Z-2-chloro-3,3,3-trifluoroprop-1-en-1-yl)-2,2-dimethylcyclopropane carboxylate and its enantiomer, which may be caused to crystallize out from the solution.

6 Claims, No Drawings

INSECTICIDAL PRODUCT AND PREPARATION THEREOF

This invention relates to an insecticidal product and methods of preparing it.

The compound α-cyano-3-phenoxybenzyl cis-3-(Z-2-chloro-3,3,3-trifluoroprop-1-en-1-yl)-2,2-dimethylcyclopropane carboxylate, also known by its common name of cyhalothrin, its preparation and insecticidal use is described inter alia in U.S. Pat. No. 4,183,948. This product is a mixture of four isomers which may be conveniently described as follows:

Isomer A—the ester derived from the (+)-cis-acid and the α-(S)-alcohol.
Isomer B—the ester derived from the (−)-cis-acid and the α-(R)-alcohol.
Isomer C—the ester derived from the (+)-cis-acid and the α-(R)-alcohol.
Isomer D—the ester derived from the (−)-cis-acid and the α-(S)-alcohol.

Cyhalothrin itself contains typically from 40–60% by weight of isomers A and B and 60–40% by weight of isomers C and D and is a viscous liquid at the ambient temperature. It cannot be induced to crystallise by cooling.

Now isomer A and isomer B have identical physical properties, eg. solubility, melting point, etc., differing only in the direction in which they rotate the plane of polarised light, and as such represent a pair of enantiomers. Similarly, isomer C and isomer D represent a second enantiomeric pair.

It is known from P. D. Bentley et al, Pestic. Sci., 11, (2), 156–64 (1980) that Isomer A is the most active insecticide of the four isomers and that isomers B and D were insecticidally inactive in tests against houseflies (*Musca domestica*). Isomer A is in fact about 25 times more active than the known insecticide permethrin in this test, making it one of the most active synthetic insecticides yet reported. Although it would be desirable to use isomer A alone as the active ingredient of insecticidal preparations, this is not easy to achieve in an economical manner because this requires that the acid and alcohol moieties of the isomer be prepared by chiral synthetic techniques and reacted together in a manner which does not change the chirality. Such techniques have not yet been developed to a level where such a synthesis can be carried out in an economic manner without the co-production of unwanted isomeric products which require to be separated using expensive reagents.

A technique has recently been developed whereby the pair of enantiomers represented by isomer A and isomer B can be readily separated from isomer C and isomer D by physical means not requiring chiral synthesis or chemical resolution, and that insecticidal products of acceptable efficacy can be prepared in an economic manner using the enantiomer pair.

This technique provides a process for obtaining a crystalline material (hereinafter called "the Product") consisting essentially of the enantiomeric pair of isomers represented by (S)-α-cyano-3-phenoxybenzyl (1R,cis)-3-(Z-2-chloro-3,3,3-trifluoroprop-1-en-1-yl)-2,2-dimethylcyclopropane carboxylate and (R)-α-cyano-3-phenoxybenzyl (1S,cis)-3-(Z-2-chloro-3,3,3-trifluoroprop-1-en-1-yl)-2,2-dimethylcyclopropane carboxylate in racemic proportions and substantially free from any other isomer of α-cyano-3-phenoxybenzyl 3-(2-chloro-3,3,3-trifluoroprop-1-en-1-yl)-2,2-dimethylcyclopropane carboxylate, which comprises the steps of:-

(a) forming a solution of cyhalothrin with an organic solvent selected from lower alkanols containing up to 6 carbon atoms and liquid alkanes containing up to 8 carbon atoms, (b) cooling the solution to a temperature within the range −20° C. to +10° C. and optionally adding a quantity of crystals of the enantiomeric pair of isomers to the cooled solution, the added crystals remaining thereafter in the solid undissolved state, (c) maintaining the solution at a temperature within the said range for a sufficient period to allow the crystalline material to precipitate from the solution, (d) separating the precipitated crystalline material from the solution, and (e) optionally, if required, subjecting the crystalline material to recrystallisation.

By 'substantially free' is meant that not more than 10% by weight of the Product is represented by the combined weight of any other isomers of cyhalothrin.

Preferred alkanol solvents are ethanol, iso-propanol, butan-1-ol, butan-2-ol, pentan-1-ol, and iso-propanol/t-butanol (1:1), isopropanol/1,2-ethanediol (2:1). Isopropanol is particularly preferred. Preferred liquid alkane solvents are n-hexane and n-heptane.

By a concentrated solution is meant preferably one containing from 2:1 to 1:5, and most preferably 1:1, parts by weight of cyhalothrin: solvent.

The cyhalothrin used in this process may be contaminated with up to 10% by weight of the corresponding trans isomers and (E)-isomers. Preferably cyhalothrin of at least 95% purity is used since this usually provides the Product in higher yield and purity.

If the process is performed using a quantity of added crystals of the enantiomeric pair of isomers this usually shortens the time required to effect precipitation of the Product from the solution. (A quantity of the enantiomer pair of isomers of sufficient purity to be added may be obtained by subjecting cyhalothrin to high performance liquid chromatography (HPLC) to separate the desired enantiomeric pair of isomers from the other isomers present).

The process is preferably conducted by preparing the solution using slight warming if necessary, and then cooling the solution to a temperature in the range 0° to 10° C. for a first period during which time a substantial amount of Product crystallises, and thereafter further cooling the solution to a temperature in the range −15° to −5° C. for a second period until crystallisation is substantially complete before collecting the precipitated Product.

If recrystallisation is required to free the Product from other isomers which may have coprecipitated with the Product this may be achieved by using any suitable recrystallisation solvent, for example, the solvents referred to above as useful in the process for obtaining the Product.

We have now discovered that the yield of Product may be substantially enhanced if at least step (c) of the above process is carried out in the presence of a base. This yield enhancement is the result of conversion by epimerisation of the enantiomeric pair of isomers represented by (R)-α-cyano-3-phenoxybenzyl (1R,cis)-3-(Z-2-chloro-3,3,3-trifluoroprop-1-en-1-yl)-2,2-dimethylcyclopropane carboxylate and (S)-α-cyano-3-phenoxybenzyl (1S,cis)-3-(Z-2-chloro-3,3,3-trifluoroprop-1-en-1-yl)-2,2-dimethylcyclopropane carboxylate to form in solution the enantiomeric pair of isomers represented by (S)-α-cyano-3-phenoxybenzyl (1R,cis)-3-(Z-2-chloro-3,3,3-trifluoroprop-1-en-1-yl)-2,2-dimethylcyclopropane carboxylate and (R)-α-cyano-3-phenoxybenzyl (1S,cis)-3-(Z-2-chloro-3,3,3-trifluoroprop-1-en-1-yl)-2,2-dimethylcyclopropane carboxylate, which is thereafter precipitated from solution as Product.

In its simplest form the present invention provides a process for the relative enrichment of a solution of α-cyano-3-phenoxybenzyl 3-(Z-2-chloro-3,3,3-trifluoroprop-1-en-1-yl)-2,2-dimethylcyclopropane carboxylate with respect to the enantiomeric pair of isomers represented by (S)-α-cyano-3-phenoxybenzyl (1R,cis)-3-(Z-2-chloro-3,3,3-trifluoroprop-1-en-1-yl)-2,2-dimethylcyclopropane carboxylate and (R)-αcyano-3-phenoxybenzyl (1S,cis)-3-(Z-2-chloro-3,3,3-trifluoroprop-1-en-1-yl)-2,2-dimethylcyclopropane carboxylate which comprises subjecting a solution comprising the enantiomeric pair of isomers (R)-α-cyano-3-phenoxybenzyl (1R,cis)-3-(Z-2-chloro-3,3,3-trifluoroprop-1-en-1-yl)-2,2-dimethylcyclopropane carboxylate and (S)-α-cyano-3-phenoxybenzyl (1S,cis)-3-(Z-2-chloro-3,3,3-trifluoroprop-1-en-1-yl)-2,2-dimethylcyclopropane carboxylate to the action of a base to effect epimerisation.

Alcohols such as those specified above are suitable solvents for this process. Isopropanol is particularly preferred. The base may be any organic or inorganic base which is stable under the reaction conditions. Organic amines, especially secondary and tertiary amines, and heterocyclic bases are useful, for example triethylamine, diisopropylamine, dibutylamine, and 2,2,6,6-tetramethylpiperidine. Diisopropylamine is particularly preferred as it provides a high degree of epimerisation whilst minimising the amount of decomposition of cyhalothrin during the process. This decomposition appears to be mainly due to base-catalysed transesterification reactions involving the solvent alcohol. Another useful base is 1H-1,5,9-triazabicyclo[4,4,0]dec-9-ene having the formula:

Also useful are inorganic bases such as alkali and alkaline earth metal hydroxides and carbonates, and alkali metal salts with weak organic acids such as acetic acid. Anhydrous potassium carbonate and potassium acetate are particularly preferred.

In an especially preferred embodiment of this process a solution of cyhalothrin is passed through a column containing anhydrous potassium carbonate to effect the epimerisation.

The process is particularly useful to effect the enrichment of mother liquors from which the Product has been crystallised by the technique set out hereinabove. By the use of the combined enrichment and crystallisation processes all the cyhalothrin present may be effectively recovered in the form of the desired enantiomer pair.

In a further aspect therefore the invention provides an improved process for obtaining the Product which comprises the steps of:

(a) forming a solution of cyhalothrin with an organic solvent selected from lower alkanols containing up to 6 carbon atoms and liquid alkanes containing from 5 to 8 carbon atoms, (b) cooling the solution to a temperature within the range −20° C. to +10° C. and optionally adding a quantity of crystals of the enantiomeric pair of isomers to the cooled solution, the added crystals remaining thereafter in the solid undissolved state, (c) maintaining the solution at a temperature within the said range for a sufficient period to allow the crystalline material to precipitate from the solution, (d) separating the precipitated crystalline material from the solution, and (e) optionally, if required, subjecting the crystalline material to recrystallisation, characterised in that a base is present during at least step (c) of the process.

The Product may be precipitated in one of two different forms, hereinafter called "Product I" and "Product II". Typically Product I precipitates only slowly and the period of time required to achieve a reasonable yield is preferably at least from 7 to 15 days or even longer. Product II precipitates out much more rapidly and good yields can be achieved in a time period of from 1 to 6 days.

Where the added crystals of the enantiomeric pair of isomers were obtained by HPLC separation then the precipitate is usually in the form of Product I. If this precipitated material is recrystallised several times and then used to nucleate further crystallisations then the chances of obtaining Product II are increased, although it may be necessary to perform a number of crystallisations before Product II is actually precipitated. Product II, once obtained, when used to nucleate further crystallisations will always cause the Product to precipitate in the form of Product II.

Product I is white crystalline material having a melting point within the range 36°–42° C. when precipitated by the above process. When freed from contamination by residual amounts of isomer C and isomer D by recrystallisation Product I melts at 41°–42° C. Infra red spectral analysis shows it to consist of a conglomerate of mixed crystals in which each individual crystal is composed of molecules of a single isomer, either isomer A or isomer B, there being approximately equal amounts of crystals of each isomer. Product I is therefore a racemic mixture. These crystals are fine needles which, as indicated above, are relatively slow to crystallise out even from concentrated solutions of cyhalothrin. Collecting the Product by filtration can also be slow due to the tendency of the fine needles to clog the filter.

Product II is characterised by having a melting point above 47° C., typically 48 to 50° C. This form crystallises out more rapidly and the crystals are rhomboid-like in shape but are in fact monoclinic. This permits easier collection by filtration since the crystals of this form do not tend to clog the filter in the manner of the needles of the lower melting form described above.

Infra-red spectroscopic and X-ray crystallographic analysis of this higher melting form indicate that each individual crystal is composed of equal amounts of isomer A and isomer B arranged regularly in the crystal lattice. This form is thus a racemic compound.

Data concerning the crystalline form of Product II was collected by examining the X-ray diffraction characteristics of a crystal of dimensions ca.

0.13×0.13×0.12 mm using a Philips PW1100 four circle X-ray diffractometer with Mo-K$_\alpha$ radiation from a graphite monochromator. A $\theta$–$2\theta$ scan mode was used with a scan speed of $0.5s^{-1}$, a scan width of $0.8°$ and reflections with $3<\theta<25°$ were examined using the technique described by K. R. Adam et al, *Inorg. Chem.*, 1980, 19, 2956. The data obtained for Product II may be summarised as follows:-

Crystal form: monoclinic
Space Group: C2/c
a=34.764(5), b=7.023(2), c=18.624(3) Å
$\beta$=101.95(3)°, U=4448.46 Å$^3$, Z=8
Density=1.343 g.cm$^{-3}$, F(000)=1856.
(Mo-K$_\alpha$)=1.77 cm$^{-1}$, (Mo-K$_\alpha$)=0.71069 Å

The crystal lattice consists of regularly packed alternate molecules of the two isomers A and B, each with the trifluoromethyl group trans to the cyclopropane group across the double bond (ie. the Z-configuration). The unit cell contains 4 molecules of each enantiomeric isomer.

The Product may be formulated into insecticidal compositions which may be useful to combat and control insect pests. Except for the active ingredient these preparations and methods are identical to those preparations and methods set forth in U.S. Pat. No. 4,183,948 referred to above, the disclosure of which is herein incorporated by reference.

The invention is illustrated by the following Examples.

In the Examples, isomer A is referred to as the 1R,cis-S isomer, ie. the isomer having the (R) configuration at the carbon atom of the cyclopropane ring attached to the carboxylate group, cis referring to the relationship between the two hydrogen atoms on the cyclopropane ring and having the (S) configuration at the carbon atom bearing the cyano group. Isomer B is referred to the 1S,cis-R isomer, isomer C as the 1R,cis-R and isomer D as the 1S,cis-S isomer. Examples 1 to 3 illustrate the separation of the Product from solutions in which no base is present and do not form part of this invention.

EXAMPLE 1

This Example illustrates the separation of α-cyano-3-phenoxybenzyl cis-3-(Z-2-chloro-3,3,3-trifluoroprop-1-en-1-yl)-2,2-dimethylcyclopropane carboxylate into its constituent pairs of enantiomeric isomers.

The material to be separated was characterised by thin layer chromatographic separation of a sample on 0.25 mm (analytical grade) silica gel plates using various eluents. There was slight separation of two components corresponding to the two pairs of enantiomers present. The mean R$_f$ values for the two components were as follows:

| Eluent<br>Diethyl ether:n-hexane | R$_f$<br>(average) | $\Delta$ R$_f$ |
| --- | --- | --- |
| 10:90 | 0.22 | 0.025 |
| 15:85 | 0.28 | 0.030 |
| 20:80 | 0.33 | |

Separation of the material was achieved by use of high performance liquid chromatography using a Waters Associates System 500 apparatus fitted with a "Prep-PAK-500" silica column. This was loaded with 0.5 g of cyhalothrin consisting of a 55:45 mixture of the 1S,cis-S/1R,cis-R: 1R,cis-S/1S,cis-R enantiomer pairs. The eluent was diethyl ether/petroleum ether (boiling range 40°–60° C.) mixture (1:9) and the flow rate was 0.2 liters per minute. Fractions were collected after four recycles. The first fraction was identified by proton magnetic resonance spectroscopy as the 1S,cis-S/1R,cis-R enantiomer pair and the second fraction as the 1R,cis-S/1S,cis-R enantiomer pair. Each fraction had a purity of ca. 98% and corresponded to about 60% of the amount injected. The p.m.r. data is set out as follows ($\delta$ values in CDCl$_3$):

| 1R,cis-S/1S,cis-R | | 1S,cis-S/1R,cis-R | |
| --- | --- | --- | --- |
| 1.21<br>1.30 } | (d) | 1.34 | (s) |
| 1.98<br>2.07<br>2.19<br>2.29<br>2.38 } | (m) | 1.98<br>2.07<br>2.19<br>2.29<br>2.38 } | (m) |
| 6.38 | (s) | 6.32 | (s) |
| 6.77<br>6.87 } | (d) | 6.77<br>6.87 } | (d) |
| 6.97–7.50 | (m) | 6.97–7.5 | (m) |

EXAMPLE 2

This Example illustrates the crystallisation of the 1R,cis-S/1S,cis-R enantiomer pair from a solution of cyhalothrin. The crystals used for seeding were obtained by the process of Example 1 above.

455.6 g of a mixture of cis-isomers of α-cyano-3-phenoxybenzyl 3-(Z-2-chloro-3,3,3-trifluoroprop-1-en-1-yl)-2,2-dimethylcyclopropane carboxylate, containing 43.2% by weight of the 1R,cis-S and 1S,cis-R isomers and 56.8% by weight of the 1S,cis-S and 1R,cis-R isomers was dissolved in 460 ml of isopropanol that had been previously dried by distillation from calcium hydride. Dissolution was effected by warming the mixture to approximately 50° C. The solution was cooled to 3° C. whilst stirring with a polytetrafluoroethylene coated magnet, then seeded with a few crystals of a mixture of 1R,cis-S and 1S,cis-R isomers of α-cyano-3-phenoxybenzyl 3-(Z-2-chloro-3,3,3-trifluoroprop-1-en-1-yl)-2,2-dimethylcyclopropane carboxylate. Stirring was continued at that temperature for 9 days then the suspension cooled to $-10°$ C. and stirred vigorously with a polytetrafluoroethylene paddle for 7 days.

The solid which had separated out was filtered off at 3° C., sucked dry, washed once with 100 ml of 40°–60° petroleum ether at 3° C. and dried to constant weight in a vacuum dessicator over phosphorus pentoxide to give 97.6 g of white crystals. This product was shown by capillary gas liquid chromatography to contain 86.9% by weight of a 1:1 mixture of the 1R,cis-S and 1S,cis-R isomers of the starting material. The solid was dissolved in 300 ml of dry 40°–50° petroleum ether, the solution cooled to 3° C. with stirring and a few crystals of a mixture of 1R,cis-S and 1S,cis-R isomers of α-cyano-3-phenoxybenzyl 3-(Z-2-chloro-3,3,3-trifluoroprop-1-en-1-yl)-2,2-dimethylcyclopropane carboxylate, added as seed. After 2 hours the resultant white suspension was filtered at 3° C. and the solid sucked dry. Further drying in a vacuum dessicator over phosphorus pentoxide gave 73.6 g of a white solid containing 92% by weight of a mixture of the 1R,cis-S and 1S,cis-R isomers of α-cyano-3-phenoxybenzyl 3-(Z-2-chloro-3,3,3-trifluoroprop-1-en-1-yl)-2,2-dimethylcyclopropane carboxylate, melting in the range 36°–42° C.

EXAMPLE 3

A mixture of cyhalothrin isomers consisting of 6.4 g of the 1R,cis-S isomer, 6.4 g of the 1S,cis-R isomer, 3.2 g of the 1S,cis-S isomer and 3.2 g of the 1R,cis-R isomer was dissolved in n-hexane (20 ml) and stirred under a nitrogen atmosphere whilst maintaining the temperature at $-5°$ C. After dissolution and cooling a few milligrams of the racemic mixture (obtained by the process of Example 2 and further purified by recrystallisation until the melting point was 41.5°–42.0° C.) was added and the stirring continued for 16 hours at $-5°$ C. The precipitated solid was collected by filtration on a sintered glass funnel cooled to 0° C. and washed twice with hexane cooled to $-5°$ C. There was thus obtained 9.30 g of a material m.p. 48°–49.5° C. having a purity of at least 99% with respect to cyhalothrin isomers and consisting of at least 96.3% of the 1R,cis-S and 1S,cis-R isomers in equal proportions.

Infra red analysis indicates it to be different from the product of Example 2. The crystalline form is also different (rhomboid rather than needles) and this together with the higher melting point indicates it to be the racemic compound in which individual crystals contain equal amounts of the 1R,cis-S and 1S,cis-R isomers, both molecules being disposed in a regular arrangement throughout the crystal lattice.

Infra red (liquid paraffin mull): 1050, 1030, 1010, 990, 970 (shoulder) 963, 950, 935, 920, 908, 904, 895, 888, 873, 838, 830 (shoulder) 820, 805, 795, 785, 760, 748, 725, 702, 695, 650 cm$^{-1}$.

EXAMPLE 4

This illustrates the enrichment of cyhalothrin solutions in respect of the 1R,cis-S/1S,cis-R enantiomer pair.

After crystallisation and separation of the Product by the method of Example 2 the combined filtrate and washings were concentrated by removal of the solvents under reduced pressure and the residual oil was determined by capillary gas-liquid chromatography (using an OV 1701 column at 205° C.) as comprising α-cyano-3-phenoxybenzyl 3-(Z-2-chloro-3,3,3-trifluoroprop-1-en-1-yl)-2,2-dimethylcyclopropane carboxylate (ca. 97% by weight) consisting of ca. 33% by weight of the 1R,cis-S/1S,cis-R enantiomer pair and ca. 67% by weight of the 1R,cis-R/1S,cis-S enantiomer pair.

Aliquots (1.0 g) of this material were dissolved in isopropanol (1.3 ml) at the ambient temperature and treated with various organic and inorganic bases (0.1 g). Samples were withdrawn at intervals, diluted with isopropanol, and the composition determined by gas-liquid chromatography. The results are given in the following Table:

| BASE | Time (mins) | Purity (%) | 1R,cis-R/ 1S,cis-S (%) | 1R,cis-S/ 1S,cis-R (%) |
|---|---|---|---|---|
| None | 0 | 97 | 67 | 33 |
|  | 40 | 98 | 68 | 32 |
|  | 1658 | 92 | 67 | 33 |
| TMP | 50 | 93 | 64 | 36 |
|  | 290 | 99 | 53 | 47 |
| TEA | 60 | 98 | 63 | 37 |
|  | 300 | 98 | 55 | 45 |
| EDIA | 135 | 98 | 63 | 37 |
|  | 1395 | 94 | 55 | 45 |
| DIBA | 150 | 98 | 62 | 38 |
|  | 1411 | 95 | 53 | 47 |
| DIA | 172 | 99 | 53 | 47 |
|  | 1431 | 97 | 53 | 47 |
| K$_2$CO$_3$ | 215 | 99 | 52 | 48 |
|  | 1648 | 97 | 53 | 47 |
| "Amberlyst" A21 | 235 | 98 | 63 | 37 |
|  | 1605 | 97 | 59 | 41 |

In the above Table the bases used are as follows:
TMP = 2,2,6,6-tetramethylpiperidine
TEA = triethylamine
EDIA = ethyldiisopropylamine
DIBA = diisobutylamine
DIA = diisopropylamine
K$_2$CO$_3$ = anhydrous potassium carbonate
"Amberlyst" A21 is a basic ion-exchange resin in the free hydroxy form. "Amberlyst" is a Registered Trade Mark.

From the results set out in the Table it is clear that some decomposition of the material occurs with certain bases (and when no base is present) if the reaction time is prolonged. In these experiments the solutions were enriched in respect of the Product to values in the range 40 to 50%.

EXAMPLE 5

This Example illustrates the use of anhydrous potassium carbonate to effect the enrichment of a cyhalothrin solution with respect to the Product.

A solution of α-cyano-3-phenoxybenzyl 3-(Z-2-chloro-3,3,3-trifluoroprop-1-en-1-yl)-2,2-dimethylcyclopropane carboxylate (3.0 g) having a purity of 97% and consisting of 33% of the 1R,cis-S/1S,cis-R enantiomer pair and 67% of the 1R,cis-R/1S,cis-S enantiomer pair, in dry isopropanol (10 ml) was applied to the top of a column containing anhydrous potassium carbonate (9 g) and isopropanol (10 ml). The material was eluted through the column using isopropanol (24 ml) at a rate of 1 ml per minute. On completion of the elution the eluate was concentrated by evaporation of the eluent under reduced pressure to yield a residual oil (2.9 g, 97%) which was shown by gas-liquid chromatography to have a purity of 99% and to consist of 47% of the 1R,cis-S/1S,cis-R enantiomer pair and 53% of the 1R,cis-R/1S,cis-S enantiomer pair.

EXAMPLE 6

This Example illustrates the improved yield of the 1R,cis-S/1S,cis-R enantiomeric pair of isomers in the invention process.

A mixture of cyhalothrin (200 parts by weight containing 42% by weight of the 1R,cis-S/1S,cis-R isomer pair and 58% of the 1S,cis-S/1R,cis-R enantiomer pair, isopropanol was charged to two round bottomed flasks containing glass beads, cooled to $-5°$ C. and crystals of the 1R,cis-S/1S,cis-R isomer pair in the racemic compound form (4 parts by weight) was added to each flask. To one flask was added 1H-1,5,9-triazabicyclo[4,4,0]-dec-9-ene (0.5 parts by weight) and then both flasks were rotated at $-5°$ C. for 1 day after which the precipitated crystalline material was collected by filtration, washed with cold hexane and dried.

The experiment to which base was added yielded 119 parts by weight of the crystalline material containing 92% by weight of the 1R,cis-S/1S,cis-R representing a yield of 68% based on cyhalothrin charged. This compared to only 39 parts by weight containing 94% by weight of the 1R,cis-S/1S,cis-R isomer pair, representing a yield of only 20% based on cyhalothrin charged for the experiment in which no base was used.

EXAMPLE 7

This Example illustrates a process for obtaining multiple crops of Product II. A vessel fitted with a polytetrafluoroethylene paddle agitator was charged with a mixture of technical cyhalothrin (100 parts by weight, purity 90.2% by weight containing 43% by weight of the 1R,cis-S and 1S,cis-R enantiomeric pair of isomers and 57% by weight of the 1S,cis-S and 1R,cis-R enantiomeric pair of isomers), isopropanol (100 parts by volume), and diisopropylamine (3.5 parts by weight), and the contents cooled to −2° C. after which crystals of the 1R,cis-S and 1S,cis-R enantiomeric pair of isomers (in the form of Product II, 7.5 parts by weight) was added. After a period of 3 days a proportion of the batch was discharged to the filter and a similar volume of the above pre-cooled mixture added to the vessel. After a further period this was again partially discharged to the filter and the volume loss made up with fresh mixture. This was repeated for a total of 8 cycles after which the entire batch was discharged to the filter. The product was collected by filtering through a jacketed sinter pre-cooled to 0° C. and slurry washed on the sinter using 2×0.5 bed volumes of isopropanol pre-cooled to −5° C. The product was then dried to constant weight in a vacuum dessicator and analysed to show it consisted of the 1R,cis-S and 1S,cis-R enantiomeric pair of isomers of cyhalothrin in the form of the racemic compound, melting point 49°–50° C. The details of the process are set out in the following Table from which it can be seen that at total of 1033.7 g of crystalline product was obtained, 97% (1003 g) of which represents the desired enantiomeric pair of isomers, from a charge of 1483.8 g of cyhalothrin containing 43% (638 g) of the 1R,cis-S/1S,cis-R enantiomeric pair of isomers. This indicates that at least 365 g of the recovered crystalline material was obtained by base-catalysed epimerisation of the 1R,cis-R/1S,cis-S enantiomeric pair of isomers leading to an overall yield of ca 70% with respect to cyhalothrin charged.

| Cycle No | Cyhalothrin charged (g) | Time period (days) | % of batch discharged | Wt of precipitated collected | % content of 1R,cis-S/1S,cisR isomer pair |
|---|---|---|---|---|---|
| 1 | 290.8* | 3 | 58 | 128.0 | 97 |
| 2 | 155.5 | 3 | 61 | 131.3 | 98 |
| 3 | 148.2 | 3 | 66 | 135.4 | 98 |
| 4 | 162.8 | 4 | 64 | 129.5 | 96 |
| 5 | 171.1 | 1 | 63 | 102.1 | 97 |
| 6 | 191.4 | 1 | 68 | 121.1 | 97 |
| 7 | 191.6 | 1 | 69 | 127.8 | 97 |
| 8 | 192.4 | 1 | 100 | 178.5 | 97 |

*Includes 20 g added crystals.

I claim:

1. A process for the relative enrichment of a solution of α-cyano-3-phenoxybenzyl 3-(Z-2-chloro-3,3,3-trifluoroprop-1-en-1-yl)-2,2-dimethylcyclopropane carboxylate with respect to the enantiomeric pair of isomers represented by (S)-αcyano-3-phenoxybenzyl (1R,cis)-3-(Z-2-chloro-3,3,3-trifluoroprop-1-en-1-yl)-2,2-dimethylcyclopropane carboxylate and (R)-α-cyano-3-phenoxybenzyl (1S,cis)-3-(Z-2-chloro-3,3,3-trifluoroprop-1-en-1-yl)-2,2-dimethylcyclopropane carboxylate which comprises subjecting a solution comprising the enantiomeric pair of isomers (R)-α-cyano-3-phenoxybenzyl (1R,cis)-3-(Z-2-chloro-3,3,3-trifluoroprop-1-en-1-yl)-2,2-dimethylcyclopropane carboxylate and (S)-α-cyano-3-phenoxybenzyl (1S,cis)-3-(Z-2-chloro-3,3,3-trifluoroprop-1-en-1-yl)-2,2-dimethylcyclopropane carboxylate in an organic solvent to the action of a base to effect epimerisation.

2. A process according to claim 1 wherein the organic solvent is a lower alkanol containing up to six carbon atoms.

3. A process according to claim 2 wherein the lower alkanol is isopropanol.

4. A process according to claim 1 wherein the base is secondary or tertiary amine or a heterocyclic base.

5. A process according to claim 4 wherein the base is diisopropylamine, 2,2,6,6-tetramethylpiperidine or 1H-1,5,9-triazabicyclo-[4,4,0]-dec-9-ene.

6. A process for obtaining an enhanced yield of a crystalline material consisting essentially of the enantiomeric pair of isomers represented by (S)-α-cyano-3-phenoxybenzyl (1R,cis)-3-(Z-2-chloro-3,3,3-trifluoroprop-1-en-1-yl)-2,2-dimethylcyclopropane carboxylate and (R)-α-cyano-3-phenoxybenzyl (1S,cis)-3-(Z-2-chloro-3,3,3-trifluoroprop-1-en-1-yl)-2,2-dimethylcyclopropane carboxylate in racemic proportions and substantially free from any other isomer of α-cyano-3-phenoxybenzyl-3-(2-chloro-3,3,3-trifluoroprop-1-en-1-yl)-2,2-dimethylcyclopropane carboxylate, which comprises the steps of:

(a) forming a concentrated solution of cyhalothrin with an organic solvent selected from lower alkanols containing up to six carbon atoms, (b) cooling the solution to a temperature within the range −20° C. to +10° C. and optionally adding a quantity of crystals of the enantiomeric pair of isomers to the cooled solution, the added crystals remaining thereafter in the solid undissolved state, (c) maintaining the solution at a temperature within the said range for a sufficient period to allow the crystalline material to precipitate from the solution, (d) separating the precipitated crystalline material from the solution, and (e) optionally, if required, subjecting the crystalline material to recrystallisation, characterised in that a base is present during at least step (c) of the process whereby at least a proportion of the enantiomeric pair of isomers represented by (R)-α-cyano-3-phenoxybenzyl (1R,cis)-3-(Z-2-chloro-3,3,3-trifluoroprop-1-en-1-yl)-2,2-dimethylcyclopropane carboxylate and (S)-α-cyano-3-phenoxybenzyl (1S,cis)-3-(Z-2-chloro-3,3,3-trifluoroprop-1-en-1-yl)-2,2-dimethyl-cyclopropane carboxylate is converted to the enantiomeric pair of isomers represented by (S)-αcyano-3-phenoxybenzyl (1R,cis)-3-(Z-2-chloro-3,3,3-trifluoroprop-1-en-1-yl) -2,2-dimethylcyclopropane carboxylate and (R)-α-cyano-3-phenoxybenzyl (1S,cis)-3-(Z-2-chloro-3,3,3-trifluoroprop-1-en-1-yl)-2,2-dimethylcyclopropane carboxylate.

* * * * *